United States Patent
Wedge, Jr.

[11] Patent Number: 5,807,293
[45] Date of Patent: Sep. 15, 1998

[54] SPLINT ASSEMBLY FOR POSITIONING OF A DISABLED DISEASED, OR INJURED HAND AND WRIST

[76] Inventor: Roy D. Wedge, Jr., 4408 Cruz Dr., Midland, Mich. 48642

[21] Appl. No.: 853,888

[22] Filed: May 9, 1997

Related U.S. Application Data

[60] Provisional application No. 60/017,309, May 13, 1996.

[51] Int. Cl.⁶ .............................. A61F 5/00; A61F 5/37
[52] U.S. Cl. .............................. 602/21; 602/21; 602/64; 128/879
[58] Field of Search .................................. 602/5, 20–22, 602/62, 64, 12; 128/878–880; 2/20, 21, 160, 161.1, 162, 163

[56] References Cited

U.S. PATENT DOCUMENTS

| | | | |
|---|---|---|---|
| 1,797,057 | 3/1931 | Foulke | 602/21 |
| 2,025,357 | 12/1935 | Pagan | 2/20 X |
| 4,173,218 | 11/1979 | Cronin . | |
| 4,706,658 | 11/1987 | Cronin . | |
| 4,765,320 | 8/1988 | Lindemann et al. . | |
| 5,121,743 | 6/1992 | Bishop | 128/879 X |
| 5,248,292 | 9/1993 | Holland | 602/20 X |
| 5,295,948 | 3/1994 | Gray | 602/20 X |
| 5,388,273 | 2/1995 | Sydor et al. | 2/255 |
| 5,397,296 | 3/1995 | Sydor | 602/21 |
| 5,409,447 | 4/1995 | Wedge, Jr. | 602/21 X |
| 5,476,439 | 12/1995 | Robinson | 128/879 X |
| 5,560,375 | 10/1996 | Kabanek | 128/879 X |
| 5,637,078 | 6/1997 | Varn | 128/879 X |

*Primary Examiner*—Richard J. Apley
*Assistant Examiner*—Denise Pothier
*Attorney, Agent, or Firm*—Miller, Johnson, Snell & Cummiskey, P.L.C.

[57] ABSTRACT

A splint assembly is provided for use by health professionals in the positioning of a human hand. The arrangement includes a splint which is made of thermoplastic material in the shape of a hand, with open spaces between the fingers and thumb so that a glove may be placed simultaneously over the hand and splint for positioning of the hand. The cross-sectional shapes of the finger and wrist support areas resist movement of the fingers and wrist with the resistance increased or decreased by selection of thermoplastics with a higher or lower modulus of elasticity. A splint cover, made of a moisture absorbent material, acts as a cushion and prevents direct contact of the skin of the hand with the plastic material of the splint. An outer glove covering, made of a combination of stretch and/or non-stretch material, serves to maintain the position of the hand in the splint.

17 Claims, 3 Drawing Sheets

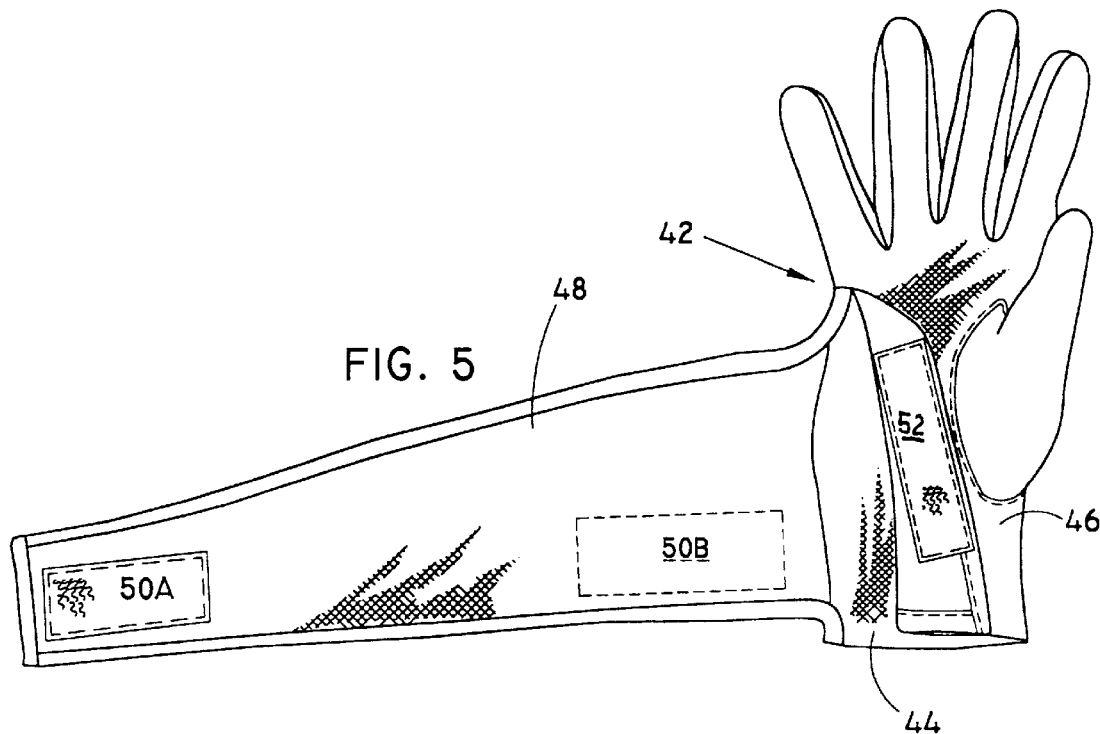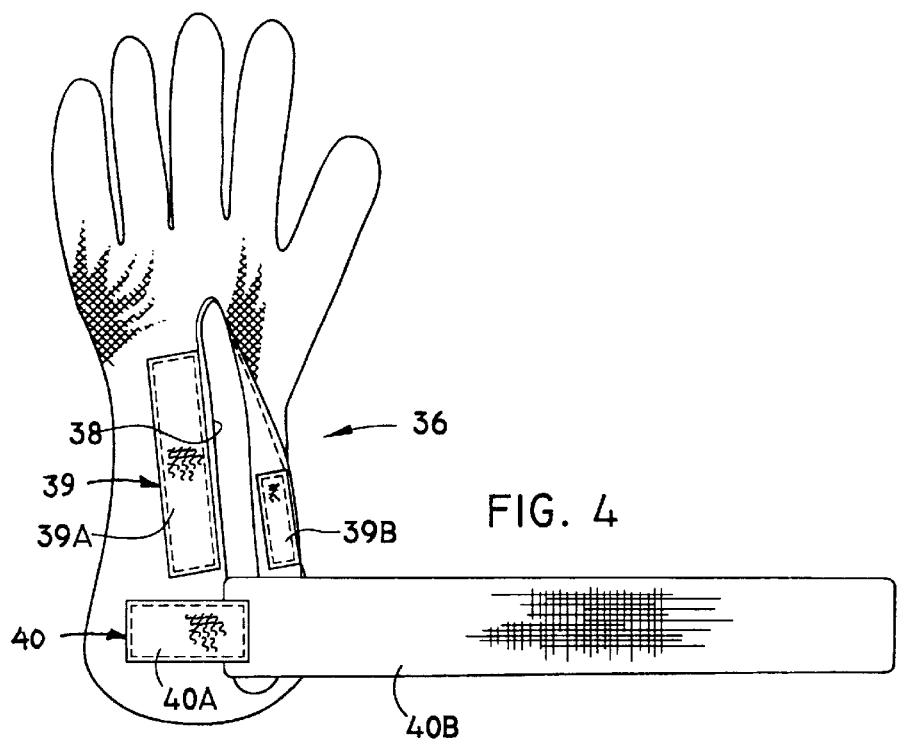

SPLINT ASSEMBLY FOR POSITIONING OF A DISABLED DISEASED, OR INJURED HAND AND WRIST

CROSS-REFERENCE TO RELATED APPLICATION

This application claims the benefit of U.S. Provisional application Ser. No. 60/017,309 filed May 13, 1996.

1. Field of the Invention

This invention, hereinafter referred to as the splint assembly relates to a human hand splinting and/or orthopedic assembly device used to position a disabled, diseased, or injured human hand.

2. Description of the Prior Art

A hand splint or wrist hand orthosis is used to position a human hand that is disabled, diseased, or injured. These splints are usually formed out of plastic materials and are provided with straps that allow for easy donning and doffing. As technology improved and suitable low temperature thermoplastics were made available, fitting of the splints directly against the patient's skin became feasible. Hand splints are used in many different forms to position hands and fingers for protection, optimal functional use, and to prevent problems of contractures and edema. Many splints used today are hand formed and custom fit to patients by qualified occupational or physical therapists. All of these splints provide for support and positioning of a disabled hand. The position of the wrist, fingers, and thumb is usually maintained by VELCRO® brand straps of soft material that wrap around the hand. Various types of foam splint liners and hand coverings are used to increase the comfort of the splint. The splints are generally used in the form of a homogenous mitt or similar shape, whereby the fingers of a hand are all supported by a single platform area and the thumb is supported separately. The splint usually provides support to the wrist as well.

U.S. Pat. Nos. 4,173,218 and 4,706,658 describe gloved splints. These splints provide for positioning of a human hand for protection and healing. The gloves contain bladders that may be filled with warm or cold fluids to provide comfort to the patient. They also provide for alignment of the fingers and only allow flexibility at finger hinge points of the splint. These described structures do not mention or provide resistance to movement of the fingers and thumb, but instead focus on flexibility and functional use. One of the primary tenants of these two designs relates to allowing for flexibility at "hinge points" of the fingers. These designs do not, therefore, provide a dynamic component of resistance to movement.

Splints are often provided for patients who have suffered a stroke or other neurological damage. These splints provide support and positioning to prevent injury and resist the formation of debilitating contractures. Hypertonicity is a condition where the muscles are spastic and resist positioning efforts. Fitting of splints for patients who have hypertonicity is usually difficult, with mixed results of success. The splints being used today are generally rigid in nature, not allowing movement of the supporting structure for the wrist, fingers, and thumb. The hypertonicity of the hand and rigid nature of the splint interact poorly, often causing the fingers and thumb to pull out from under the straps being used to hold them in place.

Resting splints made for arthritic patients are generally similar to the mitt splints mentioned above. The fingers of a hand are usually kept from drifting to the ulnar side by providing a turned up edge on that side of the finger area of the splint. The fingers in this area are normally restrained by a single strap, which may allow some undesired lateral movements as fingers slide over the top of each other. Other types of strapping devices are used to individually position a user's fingers.

The dynamic "low profile" splint described in U.S. Pat. No. 4,765,320 provides for motion of the fingers with a low amplitude of force for resistance. These splints are called "low profile splints" because they are significantly less cumbersome than previous splints having a high profile of outriggers. They continue, however, to present significant problems to the wearer because of their bulky nature. For example, it is impossible to put on a coat while wearing this type of splint, and patients are generally unable to sleep while wearing it. It is common practice to provide a "night splint" for positioning at night and a "low profile" splint for day wear. A splint of this type may be used following a metacarpalphalangeal (MCP) joint replacement. Dynamic resistance is provided by rubber bands or springs attached to finger loops which pull the fingers into MCP joint extension. Alignment of fingers is maintained by positioning and adjusting of the outriggers. There is often a tendency, however, for the fingers to drift in the ulnar direction when the MCP joints are flexed, creating the need for additional straps and lines to pull the fingers back to an acceptable alignment.

The splints in conventional use today are bulky in nature, causing increased problems for the wearer while engaged in normal daily activities such as dressing. The typical resting hand mitt splint may be difficult or impossible to pass through a normal size coat sleeve, and an anti-spasticity ball splint, which is used to reduce hypertonicity, is even more bulky.

Edema gloves are commonly used to reduce swelling of a disabled hand. These gloves, however, are difficult to place on the affected hand of a patient who has abnormal tone.

It is the intent of this invention to provide occupational therapists and physical therapists with a unique alternative to the standard types of hand splints being used today. The splint assembly takes advantage of the elastic nature of both the splint and the glove to provide improved positioning of the human hand.

SUMMARY OF THE INVENTION

A splint assembly is provided for supporting the user's wrist in a neutral or relatively extended configuration with the user's phalanges in a normal functional position. The splint assembly includes a resilient splint member having a forearm portion, a wrist portion, a palm portion, and a phalange portion, the phalange portion including a plurality of individual phalange supports. The resilient splint member is adapted to receive the volar surface of the user's forearm, wrist, palm, and phalanges, with the palm portion having longitudinal ridges equal in number to the phalange supports, each longitudinal ridge radiating from a point proximate the wrist portion to a point proximate a tip of a respective one of the phalange supports. With the resilient splint member against the volar surface of the user's phalanges, palm, wrist, and forearm, a glove is provided to be received over the respective anatomical features to maintain the neutral or relatively extended configuration of the user's wrist and to maintain the user's phalanges in a normal functional position.

The splint assembly further includes a central longitudinal ridge extending along a volar side of the wrist and forearm portions of the resilient splint member for providing longitudinal rigidity to that portion of the splint. The resilient splint member is covered and enclosed by a cover which individually surrounds each of the phalange portions, palm, wrist, and forearm. The forearm portion of the cover includes a strap attached thereto, having hook-and-loop fasteners at appropriate locations for securing the resilient splint member to the forearm of the user. A glove received over the phalanges, palm, and wrist portion of the user secures the opposite end of the resilient splint member to the user.

The spreading of the phalanges (fingers and thumb) help reduce hypertonicity of an affected hand. The phalanges are positioned in the splint assembly to take advantage of this effect. The elasticity of the glove provides a dynamic component which serves to maintain the desired position of the hand in the splint and reduce hypertonicity. The glove effectively holds the hand and fingers in place using the splint as the basis of support for positioning. There is no need for tabs or other mechanical devices to maintain phalange positions.

Other advantages of the splint assembly are its size and appearance. The splint itself has less surface area than a standard splint, and the shape resembles a normal hand. The shape of the splint allows for significant reduction of material used and decreases the likelihood of excessive pressure on the hand, since the firm portion of the splint is only in contact with the volar side of the hand where there is more fleshy tissue. Rigidity provided by the cross-sectional shape of the splint at the wrist and finger support areas facilitates a small surface area on the volar side of the hand, decreasing the likelihood of encountering a bony area with the edge of the splint. Furthermore, the splint cover fits over the splint before the outer glove is applied. The cover prevents direct contact of the user's skin with the plastic of the splint, thus making the splint more comfortable and reducing the irritating "hot sticky feeling" that is sometimes associated or described. The cover also provides a barrier between the splint material and the skin of those individuals who may have an allergic reaction to plastic materials.

Hygiene is also improved for the splint assembly, since the splint cover and outer glove are easily removed for washing.

These and other features, advantages and objects of the present invention will be further understood and appreciated by those skilled in the art by reference to the following specification, claims and appended drawings.

BRIEF DESCRIPTION OF THE DRAWINGS

FIG. 4 is a plan view of a splint cover;

FIG. 5 is a plan view of the outer glove member;

DETAILED DESCRIPTION OF PREFERRED EMBODIMENT

Figure 1:
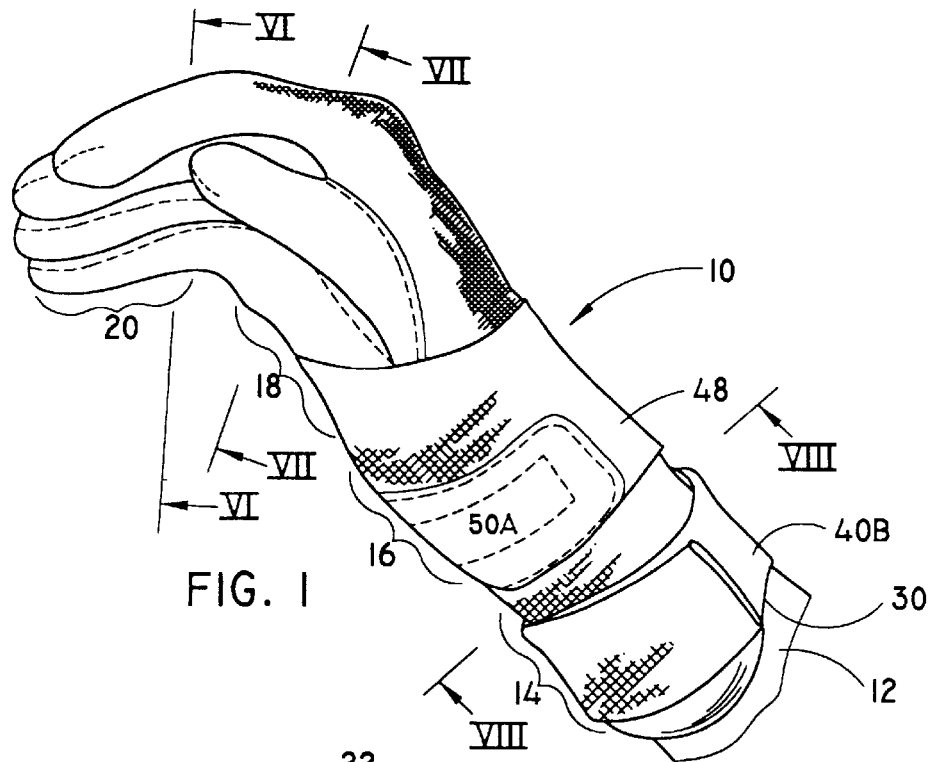
FIG. 1 is a prospective view of the splint assembly on a user.
Figure 2:
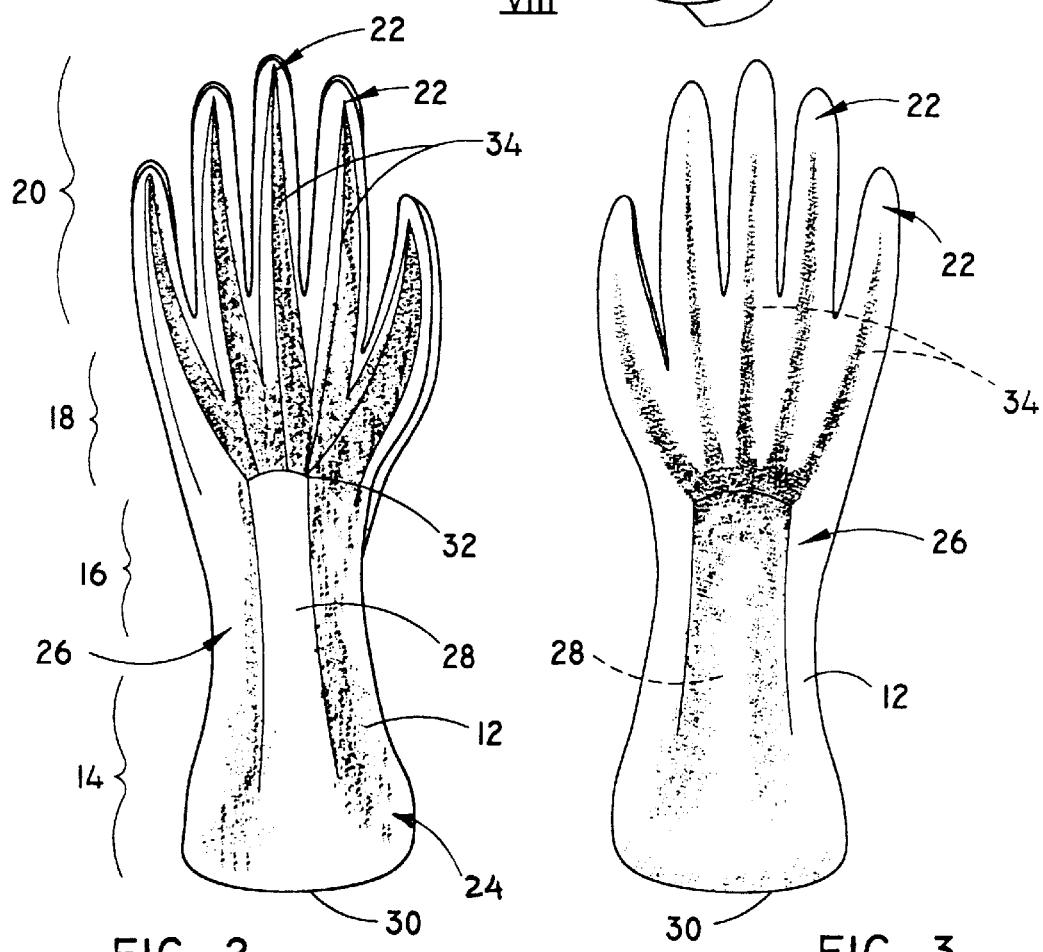
FIG. 2 is a bottom elevation view of the resilient splint member.
Figure 3:
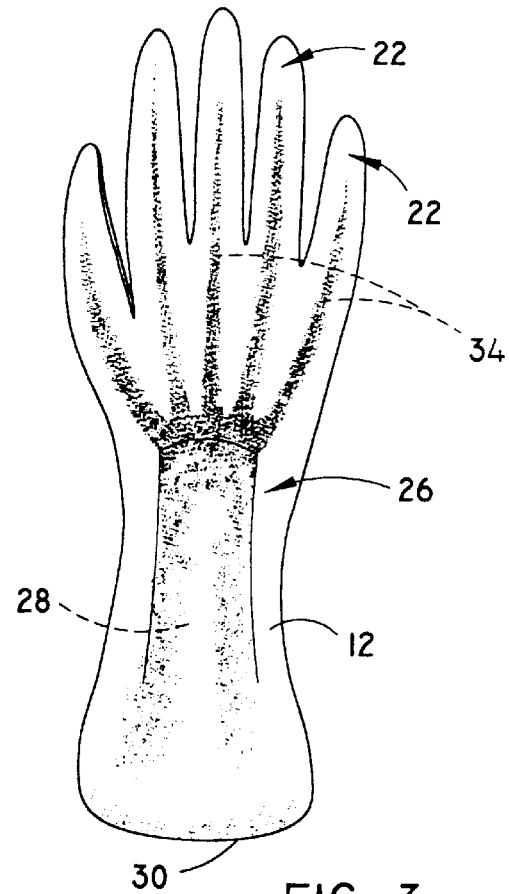
FIG. 3 is a plan view of the resilient splint member.

For purposes of the following description, references to digits or phalanges shall be the broader definitions of a user's fingers or thumb and, depending upon the context, may be used interchangeably. Where reference is made to a specific anatomical feature, that reference may also be extrapolated to the general.

In accordance with certain of its objects, this invention relates to an orthopedic positioning device for a disabled, diseased, or injured human hand which comprises a molded, semi-rigid thermoplastic support, said support to be molded in the shape of a hand and providing positioning of the wrist in a neutral to slightly extended position; the transverse and longitudinal arches of the hand are supported; the fingers are maintained in a slightly flexed position and aligned in a normal functional position; the thumb has slight radial abduction and moderate palmer abduction; the finger and thumb support areas extend distally to approximately ¼ inch past the ends of the fingers and thumb of the wearer; the finger and thumb support areas have a cross-sectional shape that provides for dynamic resistance to finger and thumb movement; the finger supports are cut back to the palmer base so as to end in the approximate location of the wearer's distal palmer crease; the cross section of the splint is shaped to increase rigidity at the base of the fingers and is gradually changed to allow more flexibility distally in the finger support area; the proximal portion of the splint is curved to conform to the forearm and extends proximally to the middle of the forearm; the area of the splint which is at the wrist is stiffened by the shape of the cross section; the splint may be adjusted by therapists in the clinic to provide custom fit; a cloth splint cover is provided to create a barrier between the plastic of the splint and the skin of the hand; the cloth of the splint cover also acts to absorb moisture; the cover is made in the shape of the splint and may be pulled over the splint; positioning straps are provided with VELCRO™ brand hook-and-loop material for fastening; the outer glove covering may be of a combination of stretch and/or non-stretch material.

The cross-sectional shapes of the finger supports and wrist support area allow movement of the wrist, fingers, and thumb, but apply a dynamic force returning them to the desired resting position. Duplication of the required cross-sectional shape is impractical in a normal clinic setting. The ability of the design to be used with a variety of thermoplastic materials, however, will allow therapists to easily adjust a preformed splint using standard practices in the clinic. Simple trimming of the width of the finger supports at the proximal end will allow therapists to reduce the resistive force that pushes the fingers back to their starting position.

The splint is designed to be used in conjunction with a hand shaped covering in the form of a glove which may be made from a variety of stretch or non-stretch material. Unlike other conventional thermoplastic wrist/hand orthoses, the splint assembly has spaces between the fingers. The shape of the splint allows a glove to be placed simultaneously over it and the hand, holding the hand firmly in the desired position. Hypertonicity of the hand will often cause the wrist, fingers, and thumb to flex with such force as to create poor positioning of the hand, even though it is supported by a rigid support platform. The wrist, fingers, and thumb often slip out from under or stretch the normal positioning straps, changing the position of the hand to one that is undesirable. The splint assembly allows the wrist, fingers, and thumb to partially flex as hypertonicity increases, but the combined dynamic action provided by the elasticity of the glove and the unique shape of the splint works to push the hand back into the desired resting position as the hypertonicity subsides. The gloved splints in U.S. Pat.

Nos. 4,173,218 and 4,706,658 do not provide this type of dynamic action.

Spreading of the fingers and the thumb helps reduce hypertonicity of an affected hand. The thumb and fingers are positioned in the splint assembly to take advantage of this effect. The elasticity of the glove provides a dynamic component which serves to maintain the desired position of the hand in the splint and reduce hypertonicity. The glove effectively holds the hand and fingers in place, using the splint as the basis of support for positioning. There is no need for tabs or other mechanical devices to maintain finger or thumb positions.

Another advantage of the splint and glove arrangement is its size and appearance. The splint itself has less surface area than a standard splint and the shape looks more like a normal hand. The shape of the splint allows for a significant reduction in the material used and decreases the likelihood of excessive pressure on the hand, since the firm portion of the splint is only in contact with the volar side of the hand where there is more fleshy tissue. The rigidity provided by the cross-sectional shape of the splint at the wrist and finger support areas facilitates the use of a smaller surface area on the volar side of the hand, decreasing the likelihood of encountering a bony area with the edge of the splint.

The splint cover fits over the splint before the outer glove is applied. The cover prevents direct contact of the wearer's skin with the plastic of the splint, thus making the splint more comfortable and cutting down on the uncomfortable "hot sticky feeling" that is sometimes described. It also provides a barrier between the splint material and the skin of those individuals who may have allergic reactions to plastic materials.

In one form of the splint assembly 10 embodying the invention and shown in FIGS. 1–8, a splint 12 is provided for supporting the volar side of a portion of the forearm, the wrist, and the palm and fingers of a user, by respective portions identified generally by reference numerals 14, 16, 18, and 20. Splint 12 is cut such that individual digit supports 22 are provided to support the thumb and fingers of the user. In one embodiment, splint 12 is configured to support the user's hand in an orientation such that the wrist is in a neutral to slightly extended position. The palm portion 18 is shaped to support the transverse and longitudinal arches of the hand and places the fingers in a slightly flexed, normal functional position. The thumb is supported by one of the digit supports such that the user's thumb has a slight radial abduction and moderate palmer abduction. It is also preferred that the digit supports extend beyond the ends of the user's thumb and fingers by approximately ¼ inch. Specific features of the splint can be modified by the therapist if desired.

Figure 6:
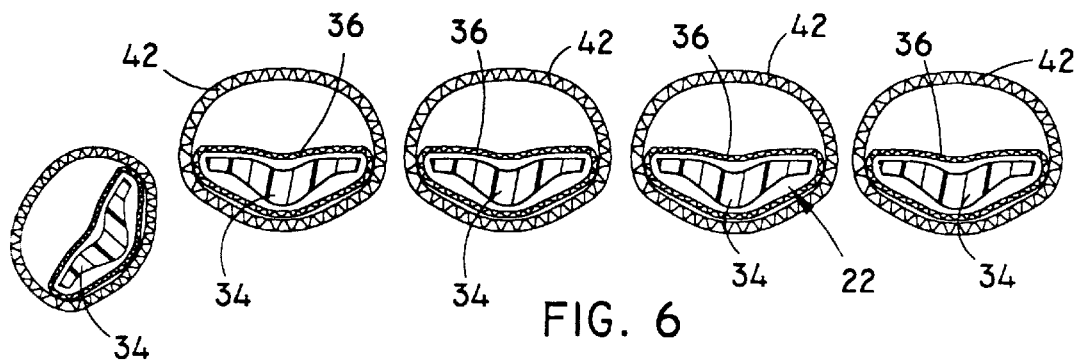
FIG. 6 is a transverse section view of the phalange supports taken along line VI—VI in FIG. 1.
Figure 7:
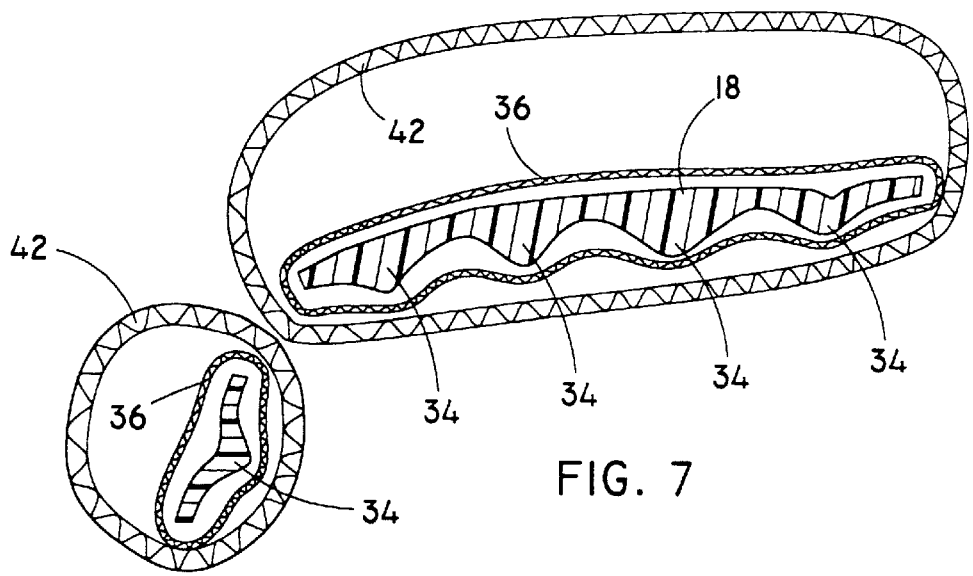
FIG. 7 is a transverse section view of the resilient splint member taken along line VII—VII in FIG. 1.
Figure 8:
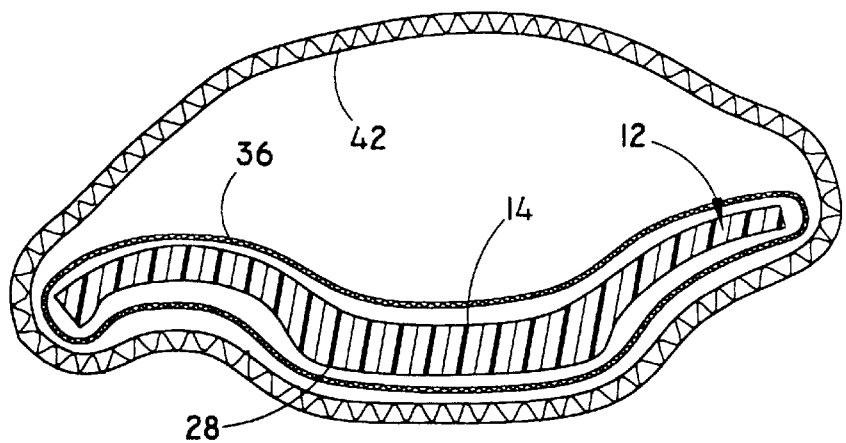
FIG. 8 is a transverse section view of the resilient splint member taken along line VIII—VIII in FIG. 1.

The transverse cross sections of splint 12 shown in FIGS. 6–8 illustrate the structures responsible for providing the dynamic flexibility in supporting the user's wrist, palm, and digits. Referring to FIGS. 2, 3, and 6–8, the proximal portion 14 of splint 12 supporting the forearm is concave along its upper surface 24 to conform to the forearm and extends longitudinally to about the middle of the forearm. The lower or volar surface 26 of the forearm portion 14 has a longitudinal rib or reinforcing member 28 preferably formed as an integral part of splint 12, ridge 28 becoming more pronounced from the proximal end 30 toward the wrist portion 16 and terminating at a junction 32 between the palm and wrist portions 18 and 16, respectively. Extending from junction 32, across the bottom surface 26 of the palm portion 18 and along each digit support 22 are longitudinal ribs 34.

In the preferred embodiment, ribs 34 are also formed as an integral part of splint 12. However, it is contemplated that external components could be attached to lower surface 26 of splint 12 to provide a similar function. In the preferred embodiment, the height or thickness of ribs 34 are greatest between junction 32 and approximately a mid-point along digit support 22. From the mid-point to the tip of each digit support, ribs 34 gradually become thinner. The location of the longitudinal ridge and ribs 28 and 34, respectively, together with the thickness of the respective members, provide a variable degree of rigidity and resiliency for the user's hand. This resiliency is also increased and imposed in many respects by providing longer digit supports 22. As mentioned above, individual digit supports 22 are provided so that each digit may be flexed independently. Although the tips extend beyond the ends of the fingers and thumb, the proximal ends of supports 22 have been cut back into the palmer portion 18 such that they terminate converger approximately at base portion the user's distal palmer crease.

In a preferred embodiment of splint 12, low temperature thermoplastics are used to form splint 12. These types of materials are quite versatile in that they can be formed easily to the user's appendages at low temperatures, are easy to trim and cut, and are relatively light. However, other materials may also be used such as the more flexible metals, such as alloys of aluminum. In cases where metal is used, the longitudinal ridge and ribs may need to be mechanically attached to the lower surface. However, the use of metal may eliminate the need for longitudinal ribs, but will require that the metal allow flexibility and dynamic resistance to movement.

Covers such as 36 (shown in FIG. 4) may be provided to encase splint 12. In a preferred embodiment, absorbent material, such as cotton or the like, is used to produce cover 36. The material may also be slightly elastic to permit easy application and removal of the cover. The cover substantially encloses forearm portion 14, wrist portion 16, palm portion 18, and each of phalange supports 22 of the splint. An opening 38 formed in the volar side of cover 36 provides a means for inserting and removing splint 12. Hook-and-loop type fasteners 39A, 39B attached to opposite sides of opening 38 provides a closure mechanism. In a preferred embodiment, one of the fastener members 39 for the opening is substantially oversized for reasons which will become apparent below. Toward the proximal end of the cover 36 and located on the volar side is a second hook-and-loop fastener 40. Fastener 40 includes a hook member 40A attached to cover 36. Sewn to one end of hook member 40A is a loop member 40B having a length sufficient to wrap around the forearm of the user and back onto fastener 40A. The purpose of hook-and-loop fastener 40 is to locate the user's forearm with respect to the forearm portion 14 of the splint. Received over splint 12, cover 36, and the user's hand and wrist is a glove 42 which extends from a position proximal the wrist support area 16 to the ends of the phalange supports 22. As shown in FIG. 5, outer glove 42 is a combination of a dorsal piece 44 and a volar piece 46. The dorsal piece 44 is cut to the shape of a hand, with an extended area at the wrist to permit wrapping around the wrist for fastening. The volar piece 46 is also cut to the shape of a hand and is made of a material that may vary in elasticity from a material that is stretch-resistant to a material that is able to stretch in a similar way as the material of an elastic glove. FIG. 5 illustrates outer glove 42 without showing the other components of the splint arrangement. Hook-and-loop type fasteners, such as sold under the brand name VELCRO®, indicated by 50A, 50B, are provided on dorsal piece 44 to secure the user's wrist in the desired position. The volar inside portion of the outer glove has a strip of one-half of a loop material, indicated as 52 to attach to a mating strip of material 39A on the volar side of cover 36.

The above description is considered that of the preferred embodiment only. Modifications of the invention will occur to those skilled in the art and to those who make or use the invention. Therefore, it is understood that the embodiment shown in the drawings and described above is merely for illustrative purposes and not intended to limit the scope of the invention, which is defined by the following claims as interpreted according to the principles of patent law, including the doctrine of equivalents.

I claim:

1. A splint assembly for positioning a human hand, comprising:

a resilient splint member having a forearm portion, an intermediate wrist portion, and a hand portion, said hand portion including a palm portion and a plurality of phalange supports extending from said palm portion, said wrist and hand portions configured to position a user's wrist at a neutral or relatively extended position, support transverse and longitudinal arches of the user's hand, and maintain the user's phalanges in a slightly flexed, normal functional position;

a plurality of ridges defined on a volar side of said resilient splint member, extending longitudinally along a lower surface of said resilient splint member, a respective one of said plurality of ridges extending from a tip of one of said phalange supports, along said palm portion and terminating approximately at said wrist portion, said plurality of ridges providing dynamic resistance to said phalange supports, said dynamic resistance being greater proximate said palm region than at said tip of each phalange support;

a cover substantially enclosing said resilient splint member for creating a barrier between the user's skin and said resilient splint member and having at least one hook-and-loop fastener attached thereto proximate said forearm portion for attaching said resilient splint member to the user's forearm;

an elastic glove received over said phalange supports, palm portion and at least a portion of said wrist portion, for positioning and restraining a user's phalanges, palm, and wrist against said resilient splint member, said elastic glove including at least one strap for securing said elastic glove over the user's hand and said resilient splint member.

2. The splint assembly as defined in claim 1, further including a longitudinal ridge extending along a volar side of said resilient splint member from a point proximate an intersection of said palm and wrist portions to a proximal end of said forearm portion.

3. The splint assembly as defined in claim 2, wherein said phalange supports extend from said palm portion of said splint member proximate the user's distal palmer crease.

4. The splint assembly as defined in claim 3, wherein said resilient splint member is formed from at least one material selected from the group consisting of thermoplastics and metals.

5. The splint assembly as defined in claim 4, wherein said thermoplastic is a low temperature thermoplastic.

6. The splint assembly as defined in claim 4, wherein said plurality of ridges defined along said volar side of said phalange and palm portion, and said longitudinal ridge extending along said volar side of said wrist and forearm portion of said resilient splint member, are thickest proximate an intersection of said palm and said wrist portion, and thinnest at the far ends of the phalange and forearm portions.

7. The splint assembly as defined in claim 4, wherein said wrist and forearm portions include a concave ventral surface for receiving the user's forearm, and a width greater at the proximal end of the forearm portion than at said wrist portion.

8. A splint assembly for supporting a user's wrist in a neutral or relatively extended configuration and the user's phalanges in a normal functional position, comprising:

a resilient splint member having a forearm portion, a wrist portion, a palm portion, and a phalange portion, said phalange portion including a plurality of individual phalange supports, said resilient splint member adapted to receive a volar side of the user's forearm, wrist, palm and phalanges, said palm portion having longitudinal ridges equal in number to said phalange supports, each radiating proximally from said wrist portion to a point proximate a tip of a respective one of said phalange supports, and a central longitudinal ridge extending along a volar side of said wrist and forearm portion of said resilient splint member;

a cover substantially enclosing said resilient splint member including individual phalange portion, said cover also including a strap attached thereto for securing said resilient splint member to the forearm of the user; and a glove configured to be received over the phalanges, palm, and wrist and at least a portion of the user's forearm as well as respective portions of said resilient splint member to maintain the neutral or relatively extended configuration of the user's wrist, and maintain the user's phalanges in the normal functional position.

9. The splint assembly as defined in claim 8, wherein said phalange supports extend from said palm portion proximate a user's distal palmer crease.

10. The splint assembly as defined in claim 8, wherein said glove includes at least one strap configured to wrap around the user's wrist or forearm and said resilient splint member for securing said glove and said resilient splint member on the user's hand and wrist.

11. The splint assembly as defined in claim 8, wherein said resilient splint member is formed from at least one of the materials consisting of thermoplastic and metal.

12. The splint assembly as defined in claim 8, wherein said forearm and wrist portions have a concave upper surface for receiving the volar portion of the user's forearm and wrist.

13. The splint assembly as defined in claim 8, wherein each of said phalange supports decrease in degree of dynamic resistance from said palm portion to a tip of each phalange support.

14. An orthopedic positioning device for a disabled, diseased or injured human hand, comprising:

a support member, having a forearm, wrist, palm, and phalange portion, said phalange portion having at least one phalange support bottom surface of said support member having longitudinal ridges equal phalange portion, said at least one phalange support, each radiating from said palm portion to a tip of said respective phalange support for providing dynamic support to the user's phalanges and palm, said support member configured to be placed adjacent a volar side of the user's forearm, wrist, palm and phalanges;

a cover substantially enclosing said support member including said phalange portions for creating a barrier between the user's skin and the support member, said cover having a strap attached thereto for securing said support member on the user; and a glove member having phalange portions equal in number to said phalange supports on said support member and a dorsal and ventral portions, said glove member configured to be received over at least a user's phalanges, palm, and portion of the wrist as well as respective portions of said support member to maintain and align the user's phalanges, palm and wrist on said support member, said glove having at least one strap to be wrapped around the user's wrist and palm for holding said glove over the user's hand.

15. The orthopedic positioning device as defined in claim 14, wherein said palm portion provides support for transverse and longitudinal arches of the user's palm, and said phalange supports are in a relatively flexed and normal functional position.

16. The orthopedic positioning device as defined in claim 15, wherein said phalange support for the user's thumb is in a position of relatively small radial abduction and relatively moderate palmer abduction.

17. The orthopedic positioning device as defined in claim 16, wherein said phalange supports extend from said palm portion at the approximate location of the user's distal palmer crease, and are shaped such that rigidity decreases from said palm portion toward the tip of each phalange support.

* * * * *